United States Patent [19]

Solomonow et al.

[11] Patent Number: 5,628,722

[45] Date of Patent: May 13, 1997

[54] METHOD FOR MAINTAINING KNEE STABILITY OF A USER SUFFERING FROM DAMAGE OF A KNEE LIGAMENT

[76] Inventors: Moshe Solomonow, 4916 Green Acres Ct., Metairie, La. 70003; Robert D'Ambrosia, 2 Lakewood Estates Dr., New Orleans, La. 70131

[21] Appl. No.: 398,681

[22] Filed: Mar. 3, 1995

[51] Int. Cl.$^6$ ...................................................... A61F 5/00
[52] U.S. Cl. ......................... 602/26; 602/23; 607/48; 607/49; 128/774; 128/782; 128/898
[58] Field of Search .................. 607/48, 49; 601/35; 602/16, 23, 26; 128/774, 782, 898; 623/31, 32; 482/51

[56] References Cited

U.S. PATENT DOCUMENTS

| | | | |
|---|---|---|---|
| 4,569,352 | 2/1986 | Petrofsky et al. | 607/49 |
| 4,697,808 | 10/1987 | Larson et al. | 601/35 X |
| 4,711,242 | 12/1987 | Petrofsky | 607/49 |
| 4,781,180 | 11/1988 | Solomonow . | |
| 5,474,088 | 12/1995 | Zaharkin et al. | 128/782 |
| 5,476,441 | 12/1995 | Durfee et al. | 607/49 X |

FOREIGN PATENT DOCUMENTS 2186191  8/1987  United Kingdom ..................... 607/49

OTHER PUBLICATIONS

"Electronics & the Aged", *Radio Electronics*, vol. 36, No. 6, Jun. 1965, p. 29.

Renstrom, P., Arms, S., Stanwyck, T., et al., "Strain within the anterior cruciate ligament during hamstring and quadricep activity." *Am. Journal Sports Medicine* 14:83–87, 1986.

Hirokawa, S., Solomonow, M., Lu, Y., et al., "Anterior–posterior and rotational displacement of the tibia elicited by quadriceps contraction." *Am. Journal Sports Medicine* 20:299–306, 1992.

Hirokawa, S., Solomonow, M., Luo, Z., et al., "Muscular Co–Contraction and Control of Knee Stability." *J. Electromyography and Kinesiology* 1:199–208, 1991.

Solomonow, M., Baratta, R., Zhou, B., D'Ambrosia, R., "Electromyogram Coactivation Patterns of the Elbow Antagonist Muscles during Slow Isokinetic Movement." *Experimental Neurology* 100:470–477, 1988.

Baratta, R., Solomonow, M., Zhou, B., et al., "Muscular coactivation: The role of the antagonist musculature in maintaining knee stability." *Am. Journal Sports Medicine* 16:113–122, 1988.

Hagood, S., Solomonow, M., Baratta, R., et al., "The effect of joint velocity on the contribution of the antagonist musculature to knee stiffness and laxity." *Am. Journal Sports Medicine* 18:182–187, 1990.

Solomonow, M., Baratta, R., Zhou, B., et al., "The synergistic action of the anterior cruciate ligament and thigh muscles in maintaining joint stability." *Am. Journal Sports Medicine* 15:207–213, 1987.

(List continued on next page.)

*Primary Examiner*—Linda C. Dvorak

[57] ABSTRACT

The present invention is a system for maintaining knee stability of a user suffering from damage of knee ligaments. It includes a sensor feedback system for measuring abnormal physical relationships between the tibia and femur. The sensor feedback system determines whether selected conditions have been met warranting the application of electrical stimulation and provides information regarding the determination to an electronic stimulator. Electrodes are spaceably mounted on selected portions of the user's hamstring and/or quadricep muscles in electrical communication with the electronic stimulator for causing contraction of the thigh muscles at selected levels, thus providing a posteriorly and/or anteriorly directed forces to the user's upper tibial bone and preventing its instability. The sensor feedback system preferably includes an upper elongated rigid member positionable adjacent the femur; a lower elongated rigid member hingedly connected on an end thereof to an end of the upper elongated rigid member; and a sensor mounted on the rigid members.

9 Claims, 2 Drawing Sheets

OTHER PUBLICATIONS

Solomonow, M., Baratta, R., D'Ambrosia, R., "The Role of the Hamstrings in the Rehabilitation of the Anterior Cruciate Ligament–Deficient Knee in Athletes." *Sports Medicine* 7:42–48, 1989.

Solomonow, M., D'Ambrosia, R., "Neural Reflex Arcs and Muscle Control of Knee Stability and Motion." Chapter 30, In: *Ligament and Extensor Injuries of the Knee: Diagnosis and Treatment*, ed. by W.N. Scott, C.V. Mossby, Hanover, MD, 1991.

Solomonow, M., D'Ambrosia, R., "Neural Reflex Arcs and Muscle Control of Knee Stability and Motion." Chapter 6, In: *The Knee*, ed. by W.N. Scott, C.V. Mossby, Hanover, MD, 1994.

Sanchez, J., Solomonow, M., Baratta, R., et al., "Control Strategies of the Elbow Antagonistic Muscle Pair During Two Types of Increasing Isometric Contractions." *J. Electromyography and Kinesiology* 3:33–40, 1993.

Solomonow, M., et al., "The RGO Generation II: Muscle Stimulation Powered Orthosis as a Practical Walking System for Thoracic Paraplegics." *Orthopedics*, 12:1209–1315, 1989.

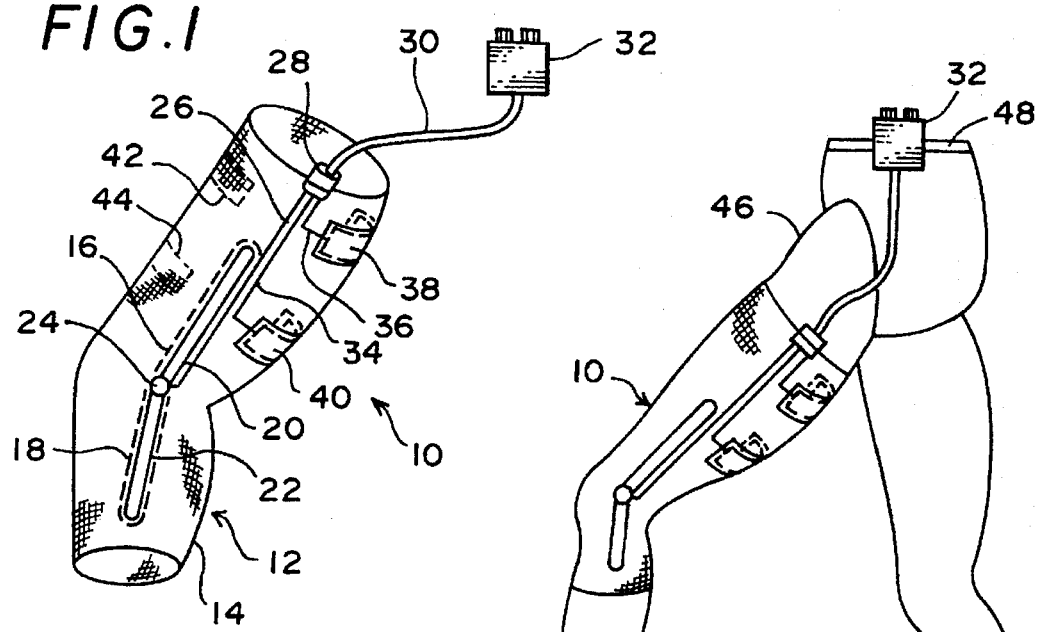
FIG. 1
FIG. 2
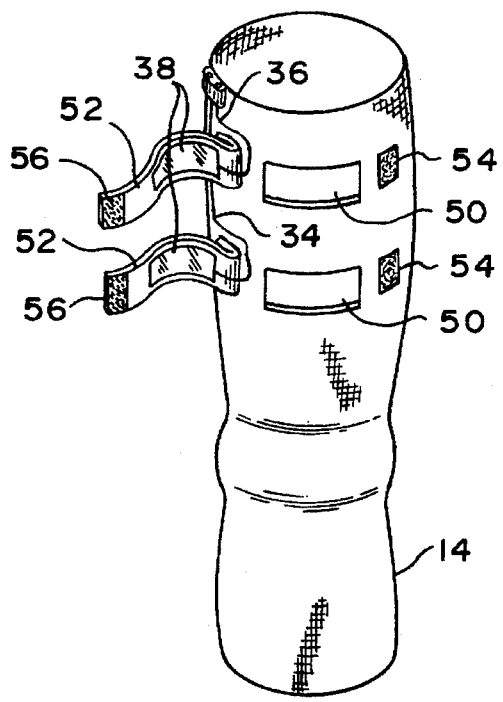
FIG. 3
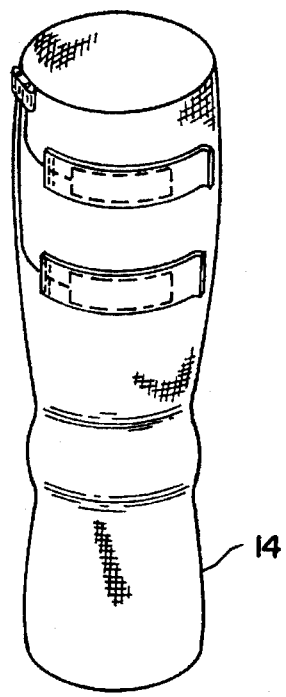
FIG. 4

FIG. 5
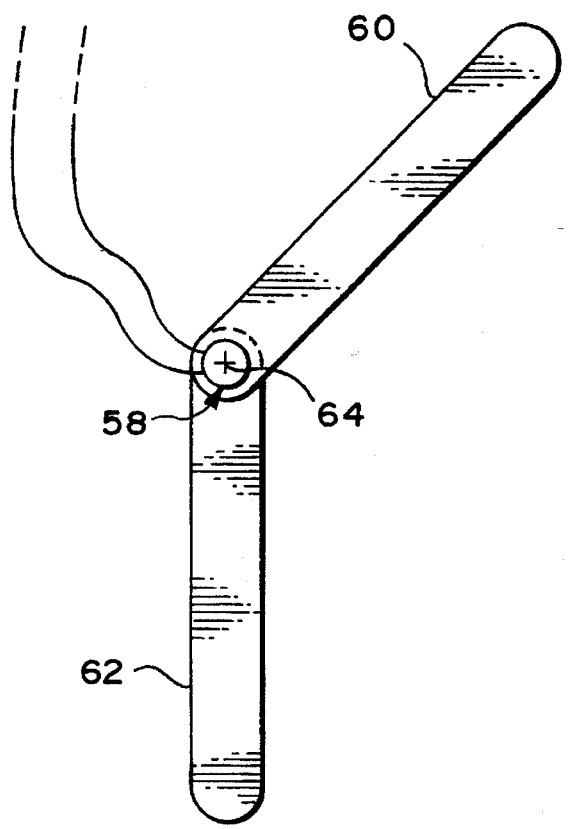
FIG. 6
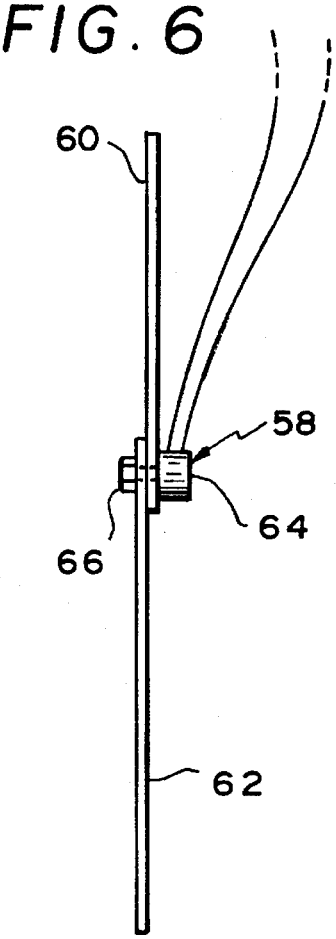
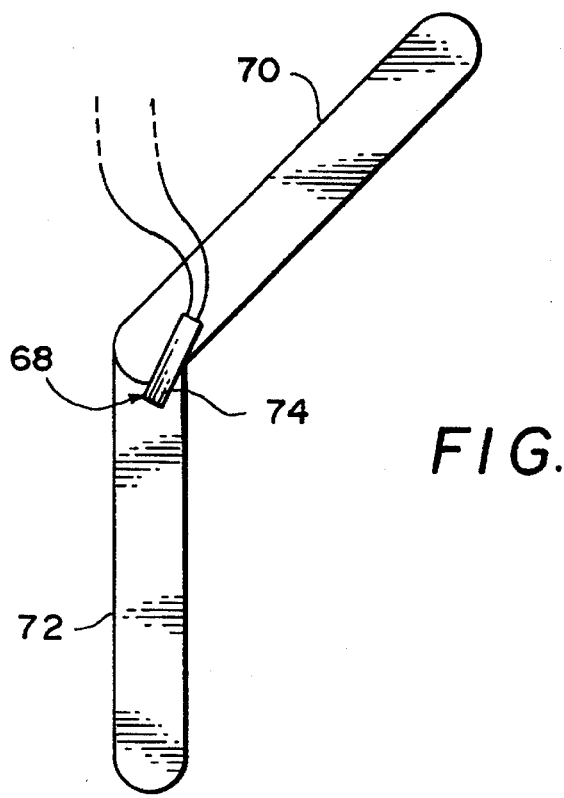
FIG. 7

METHOD FOR MAINTAINING KNEE STABILITY OF A USER SUFFERING FROM DAMAGE OF A KNEE LIGAMENT

BACKGROUND OF THE INVENTION

1. Field of the Invention

The present invention relates generally to the orthotic field and, more particularly, to systems used by patients suffering a deficiency of the knee function due to injuries of the ligaments or connective tissues.

2. Description of the Related Art

Rupture or damage to the various knee ligaments causes episodes of knee instability and difficulties during walking, climbing stairs, etc. The damaged ligaments no longer provide the upper leg bone (femur) and lower leg bone (tibia) with the necessary restraints to keep them pivoting relative to each other in the normal manner.

For example, if the anterior ligament is damaged or ruptured, the knee loses the restraining force of the tibia during the extension movement from 60° flexion into full extension. In this range of motion, the tibial bone frequently displaces forward (anteriorly), causes knee instability and loss of balance for the patient; consequently, the patient fails. Renstrom et al. have shown that the range of 60° flexion–15° extension causes an increasing strain in the anterior ligament. (See Renstrom, P., Arms, S., Stanwyck, T., et al., "Strain within the anterior cruciate ligament during hamstring and quadricep activity." *Am. Journal Sports Medicine* 14:83–87, 1986.) Hirokawa et al. have shown that indeed the tibial bone is displaced anteriorly in this range of motion and causes the strain in the ligament. (See Hirokawa, S., Solomonow, M., Lu, Y., et al., "Anterior-posterior and rotational displacement of the tibia elicited by quadriceps contraction." *Am. Journal Sports Medicine* 20:299–306, 1992.) Both Hirokawa et al. (See Hirokawa, S., Solomonow, M., Luo, Z., et al., "Muscular Co-Contraction and Control of Knee Stability." *J. Electromyography and Kinesiology* 1:199–208, 1991) and Renstrom et al. (above) have shown that mild to moderate contraction of the hamstrings can significantly reduce the anterior displacement of the tibia and the associated strain in the ligament which occurs in that range of motion.

The present applicants have shown that, during regular movement of subjects' intact healthy knees and elbows, mild to moderate contraction of the antagonist muscle (hamstrings during knee extension and triceps during elbow flexion) is the mode by which the nervous system maintains joint stability in daily movements. (See Solomonow, M., Baratta, R., Zhou, B., D'Ambrosia, R., "Electromyogram Coactivation Patterns of the Elbow Antagonist Muscles during Slow Isokinetic Movement." *Experimental Neurology* 100:470–477, 1988; Baratta, R., Solomonow, M., Zhou, B., et al., "Muscular coactivation: The role of the antagonist musculature in maintaining knee stability." *Am. Journal Sports Medicine* 16:113–122, 1988; Hagood, S., Solomonow, M., Baratta, R., et al., "The effect of joint velocity on the contribution of the antagonist musculature to knee stiffness and laxity." *Am. Journal Sports Medicine* 18:182–187, 1990.) Present applicants have also shown that such mild antagonist cocontraction could be increased in subjects and patients by training. (See Baratta, R., Solomonow, M., Zhou, B., et al., "Muscular coactivation: The role of the antagonist musculature in maintaining knee stability." *Am. Journal Sports Medicine* 16:113–122, 1988.)

Present applicants are also co-authors of other publications in this field, specifically as follows:

- Solomonow, M., Baratta, R., Zhou, B., et al., "The synergistic action of the anterior cruciate ligament and thigh muscles in maintaining joint stability." *Am. Journal Sports Medicine* 15:207–213, 1987;
- Solomonow, M., Baratta, R., D'Ambrosia, R., "The Role of the Hamstrings in the Rehabilitation of the Anterior Cruciate Ligament-Deficient Knee in Athletes." *Sports Medicine* 7:42–48, 1989;
- Solomonow, M., D'Ambrosia, R., "Neural Reflex Arcs and Muscle Control of Knee Stability and Motion." Chapter 30, In: *Ligament and Extensor Injuries of the Knee: Diagnosis and Treatment*, ed. by W. N. Scott, C. V. Mossby, Hanover, Md., 1991;
- Solomonow, M., D'Ambrosia, R., "Neural Reflex Arcs and Muscle Control of Knee Stability and Motion." Chapter 6, In: *The Knee*, ed. by W. N. Scott, C. V. Mossby, Hanover, Md., 1994; and,
- Sanchez, J., Solomonow, M., Baratta, R., et al., "Control Strategies of the Elbow Antagonistic Muscle Pair During Two Types of Increasing Isometric Contractions." *J. Electromyography and Kinesiology* 3:33–40, 1993.

Co-applicant Solomonow is the inventor of the system disclosed in U.S. Pat. No. 4,781,180, entitled "Orthotic Knee Brace System and Method." The patent discloses an orthotic knee brace system which includes frameworks interconnected by a hinge and the use of a tibia stabilizing force transfer assembly that is operably interconnected between the frameworks. The force-transfer assembly includes means for gradually increasing the posteriorly directed retaining force at the upper anterior portion of the tibia as the leg extends, thereby preventing anterior dislocation of the tibia from the knee joint. In another embodiment, the force-transfer assembly includes means for gradually increasing the anteriorly directed retaining force at the upper posterior portion of the tibia as the leg begins flexion with the retaining force reaching a maximum as the leg reaches full flexion, thereby preventing posterior dislocation of the tibia from the knee joint.

OBJECTS AND SUMMARY OF THE INVENTION

It is therefore a principal object of the present invention to provide a system which effectively provides substitution for the lost retaining force of the injured ligaments of the knee during knee movement and which maintains the knees stability in anterior, posterior and lateral orientations.

The present invention is a system for maintaining knee stability of a user suffering from damage of a knee ligament. It includes a sensor feedback system for measuring abnormal physical relationships between the tibia and femur. The sensor feedback system determines whether selected conditions have been met warranting the application of electrical stimulation and provides information regarding the determination to an electronic stimulator. Electrodes are spaceably mounted on selected portions of the user's hamstring and/or quadricep muscles in electrical communication with the electronic stimulator for causing contraction of the hamstring muscles at selected levels, thus providing a posteriorly directed force to the user's upper tibial bone and preventing its instability. The sensor feedback system preferably includes an upper elongated rigid member positionable adjacent the femur; a lower elongated rigid member hingedly connected on an end thereof to an end of the upper elongated rigid member; and a sensor mounted on the rigid members.

The sensor may be an angle sensor, an anterior/posterior displacement sensor, or a force sensor.

Other objects, advantages, and novel features will become apparent from the following detailed description of the invention when considered in conjunction with the accompanying drawings.

BRIEF DESCRIPTION OF THE DRAWINGS

FIG. 1 is a schematic left perspective illustration of the system of the present invention.

FIG. 2 is a left side perspective view of a user suffering from anterior ligament damage, wearing the system of the present invention.

FIG. 3 is a schematic rear perspective view of the system of the present invention, showing the straps open.

FIG. 4 is a schematic rear perspective view of the system of the present invention, showing the straps closed.

FIG. 5 is a side perspective illustration of an angle sensor utilized with upper and lower members in accordance with the principles of the present invention.

FIG. 6 is a front perspective of the FIG. 5 embodiment.

FIG. 7 is a side perspective illustration of a displacement (force) sensor used with upper and lower members in accordance with the principles of the present invention.

The same parts or elements throughout the drawings are designated by the same reference characters.

DETAILED DESCRIPTION OF THE PREFERRED EMBODIMENTS

Referring now to the drawings and the characters of reference marked thereon, FIG. 1 illustrates a preferred embodiment of the present invention, designated generally as 10. The present system 10 includes a sensor feedback system, designated generally 12, for measuring abnormal, physical relationships between the tibia and femur. The sensor feedback system 12 includes an elastic sleeve assembly 14 which is sized to securely fit over the user's knee joint and extending above and below the knee. The elastic sleeve is preferably formed of Spandex™ or similar material. It includes elongated pockets 16, 18. Elongated pockets 16, 18 contain an upper elongated rigid member 20 and lower elongated rigid member 22, respectively. Upper member 20 is positionable adjacent the femur. The lower member 22 is hingedly connected on an end thereof to an end of the upper elongated rigid member 20. Lower member 22 is positionable adjacent the tibia. A sensor 24 is operably mounted on the rigid members 20, 22. Sensor 24 may comprise an angle sensor for measuring knee flexion angles, an anterior/posterior displacement sensor for measuring tibia and femur relative displacements, or a force sensor for measuring an anteriorly directed tibial bone displacement force. An example of an angle sensor includes a potentiometer. An example of anterior/posterior displacement sensor includes a strain-gage assembly calibrated to indicate displacement. An example of a force sensor includes a strain-gage assembly calibrated to indicate force.

An electrical conduit 26 attaches to a connector 28 at the end of the elastic sleeve 14. The connector 28 may comprise one half of a male/female plug. This connector is attached, via cable 30, to an electrical stimulator 32. Second and third electrical connections or conduits 34, 36 are also connected to connector 28. The other ends are connected to upper and lower electrodes 38, 40.

Electrodes 38, 40 may be of the type comprising carbon impregnated rubber or gel covered foils which are generally used with commercial muscle stimulation devices. They preferably have surface areas of approximately 30–45 cm$^2$, each, adjusted according to the patient's size.

Referring now to FIG. 3, a rear view of the system 10 of the present invention is illustrated showing a preferred method of electrode attachment. The elastic sleeve 14 preferably includes rectangular window cut-outs 50 at the desirable location of the electrodes, one above and one below the motor point of the hamstrings muscles. Straps 52 are each stitched on one end thereof, to the elastic sleeve 14. The other end of each strap 52 contains a strip of adhesive material 56, commonly marketed under the trademark VELCRO™. The straps may cover each rectangular window 50. Each electrode 38 is mounted on the interior of a respective strap 52. Complementary VELCRO™ strips 54 secured to the elastic sleeve 14 provide secure attachment of each strap 52 to the sleeve 14. As illustrated in FIG. 4, each strip 52 can be flipped over its associated rectangular window 50 and fastened to VELCRO™ strips 54, allowing the electrode 38 to cover it while in direct contact with the skin's surface.

In the embodiment shown in FIG. 1, the electrodes are shown placed in space relationship at upper and lower portions of the hamstring portions of the elastic sleeve 14. As will be discussed below in detail, instead of or in addition to being positioned at the hamstring muscle portion of the elastic sleeve 14, electrodes may be positioned at quadricep positions, designated 42, 44.

In the case of the angle sensor mounted on the knee (which is preferable for patients with severe cases of knee instability), as the knee extends past 60°, the voltage signal from the sensor is perceived by a calibration circuit controlling a switch which is normally "off." Voltage signals which indicate smaller angles trigger the switch to the "on" condition and will activate the stimulator. Current pulses from the stimulator are conducted to the electrodes via the conduits and are passed to the muscle, thus causing it to contract mildly and provide posteriorly directed force to the upper tibia. This prevents any possible anterior instability.

The calibration circuit allows the patient to fine-tune the exact angle at which he desires the stimulator to be triggered into the "on" condition, thereby allowing any possible anatomical variation from person to person to be implemented.

Furthermore, the stimulator 32 preferably has two adjustment knobs to control stimulation pulse intensity and pulse frequency, respectively. This allows different patients with different degrees of knee instability levels to adjust the amount of force the hamstrings will apply. Generally patients with severe instabilities choose higher pulse intensities and frequencies that will elicit larger hamstring forces.

In the case of the displacement sensor mounted at the knee, a pair of strain-gages are mounted on between the upper and lower members in a bridge configuration. Once the lower rigid member placed adjacent to the tibia attempts to displace anteriorly to the equivalent of more than about 4 mm, the calibration circuit will receive the strain signal from the strain gages and will trigger the switch "on" to cause the stimulator to become activated and elicit contraction of the hamstrings and thereby prevent any further anterior displacement of the tibia.

Again, in this case, the calibration circuit has an adjustment knob that allows each patient to adjust the displacement level at which hamstrings contraction will occur, according to his degree of knee instability. Patients with severe instability may choose stimulator activation at displacement equivalent to higher than 2–3 mm, while patients with mild instability may choose activation at displacement equivalent to larger than 4–5 mm, and so on.

In the case of anterior displacement force, the sensor at the knee joint, also comprising a strain-gage bridge is calibrated to measure tibia displacement force. As the knee extends, any possible tibial anterior displacement producing more than 2 kg of force is monitored by the calibration circuit which, in turn, activates the stimulator and elicits hamstrings contraction, preventing and correcting the excessive anterior displacement force of the tibia.

Again, an adjustment knob is provided in the calibration circuit that allows patients with severe disability to trigger hamstrings contraction at lower anterior tibial displacement force, while patients with moderate or mild instability may choose hamstrings activation at higher tibial displacement forces.

Referring now to FIG. 2, the system 10 is shown applied to the leg of the user 46 suffering from damage of the anterior knee ligament. The electric stimulator 32 may be mounted on a belt 48. In this illustration, the user has two electrodes positioned on upper and lower portions of his left hamstring muscles. When the user's leg extends to a preselected level the electronic stimulator 32 causes contraction of these hamstring muscles. Thus, a posteriorly directed force is provided to the user's upper tibial bone. This prevents anterior dislocation of the tibia from the knee joint. Selected conditions that must be met warranting the application of electrical simulation may, in the case of the use of an angle sensor, comprise extension of the knee past 60° flexion. Throughout full extension an anterior/posterior displacement sensor is used for measuring tibia and femur relative displacements, the selected conditions preferably comprise relative displacement normal limits, i.e. 4–5 mm. If a force sensor is used for measuring an anteriorly directed tibial bone displacement force, the selected conditions comprise a tibial bone displacement force exceeding 2 kg.

Instead of placing the electrodes on the hamstring muscle the electrodes may be placed on the quadriceps to provide knee stability for a user suffering from deficiencies in the posterior ligaments. In such instance as the leg flexes to a predetermined level, an anteriorly directed force is applied to the user's upper tibial bone by causing contraction of the quadricep muscles, thereby preventing posterior dislocation of the tibia from the knee joint.

In instances where the user is suffering from damage to the collateral ligaments, both the hamstring and quadricep muscles may be alternatively or simultaneously stimulated to provide both anterior and posterior directed forces to the user's upper tibial bone, thus preventing its instability.

A preferred stimulator 32 generally generates rectangular, charge balanced current pulses in the intensity range of 0–140 mA. The pulse frequency ranges from 20 to 60 Hz. Both pulse intensity and frequency are adjustable to allow the patient to calibrate the most comfortable range according to the severity of the instability and the level of hamstrings contraction needed to prevent or correct the instability. In general, patients with severe instability may prefer higher intensities and frequencies of stimulation as compared to patients with milder instability.

The elongated rigid members are preferably, but not exclusively, formed of plastic material of about 1.5–2 mm thick and 2 cm wide. The length will depend on the patient's size. Taller individuals require longer elastic sleeves as well as longer rigid members.

Referring now to FIGS. 5–6, in the case where an angle sensor 58 is used, the upper and lower rigid members 60, 62 will be hingedly interconnected with the axis of the potentiometer 64 serving as the axis relative to which the rigid members 60, 62 rotate relative to each other. A nut 66 provides the necessary securement.

Referring now to FIG. 7, in the case where a displacement or displacement force sensor 68 is used, the two rigid members 70, 72 will be interconnected with a semi-rigid strip 74 of plastic on which the strain-gages are glued. As the two rigid members 70, 72 are distracted from each other by tibial instability motion, the third plastic strip 74 will be stretched, giving rise to deformation of the strain gages, and change in their electrical signal.

Generally, only two electrodes are necessary, one above and one below the muscles' motor point for optimal stimulation of the muscle. (See Solomonow, M., et al., "The RGO Generation II: Muscle Stimulation Powered Orthosis as a Practical Walking System for Thoracic Paraplegics." *Orthopedics*, 12:1209–1315, 1989)

Orthotic systems of the prior art generally consist of metallic or other rigid members fastened to the leg with elastic straps. Since the lower thigh and upper calf have an inverted cone shape, and since metallic or rigid orthoses are inherently heavy, all present orthotic systems continuously slip downward and relocate from their designated location above and below the knee and consequently lose their effectiveness. Patients attempted to solve this problem by putting great tension on the elastic strap which secured the metallic members to the leg, yet the great tension applied to the skin by the elastic straps block normal blood circulation in the skin and muscle tissue, eliciting great pain and discomfort and causing the patient to abandon use of the orthosis.

Furthermore, athletes, who constitute the majority of individuals suffering from knee ligament injuries, find that orthoses made exclusively from metallic or other rigid members are extremely dangerous in contact sports, inflicting injuries on other athletes during collision, brushing or jumping. In many sports, athletes are prohibited from using rigid knee orthoses unless they are fully coated with padding material which further increases their weight, bulk and downward slippage.

Past experience indicated that only extremely lightweight soft devices will be effective in overcoming the deficiencies of prior art devices. Hence, the present orthosis.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A method for maintaining knee stability of a user suffering from damage of a knee ligament, comprising the steps of:
   a) providing a sensor feedback system, an electrical stimulator connected to said sensor feedback system, and a plurality of electrodes connected to said electrical stimulator;
   b) mounting said plurality of electrodes on selected portions of the user's hamstring muscles;
   c) utilizing said sensor feedback system for:
      i) measuring abnormal physical relationships between the tibia and femur,
      ii) determining whether selected conditions have been met warranting the application of electrical stimulation, and
      iii) providing information regarding said determinations to an electronic stimulator; and
   d) applying electrical stimulation to said electrodes in response to said information for causing contraction of said hamstring muscles at selected levels, thus providing a posterially directed force to the user's upper tibial bone and preventing its instability.

2. The method of claim 1, wherein said step of providing a sensor feedback system, comprises providing:
   a) an upper elongated rigid member positionable adjacent the user's femur;
   b) a lower elongated rigid member hingedly connected on an end thereof to an end of said upper elongated rigid member; and
   c) a sensor mounted on said rigid members.

3. The method of claim 2, wherein said step of providing a sensor feedback system, comprises providing an elastic sleeve assembly sized to securely fit over the user's knee joint and extending above and below the knee, said elastic sleeve assembly for mounting said upper and lower elongated rigid members and said electrodes.

4. The method of claim 1, wherein said step of providing a sensor feedback system, comprises providing an angle sensor for measuring knee flexion angles.

5. The method of claim 4, wherein said step of determining whether said selected conditions have been met comprises determining whether there is extension of the knee past 60° flexion.

6. The method of claim 1, wherein said step of providing a sensor feedback system, comprises providing an anterior/posterior displacement sensor for measuring tibia and femur relative displacements.

7. The method of claim 1, wherein said step of determining whether selected conditions have been met comprises determining relative displacement exceeding normal limits.

8. The method of claim 1, wherein said step of providing a sensor feedback system, comprises providing a force sensor for measuring an anteriorly directed tibial bone displacement force.

9. The method of claim 8, wherein said step of determining whether selected conditions have been met comprises determining tibial bone displacement force exceeding normal limits.

* * * * *